(12) United States Patent
Roeder

(10) Patent No.: US 9,119,743 B2
(45) Date of Patent: Sep. 1, 2015

(54) INTRODUCER FOR DEPLOYING AN IMPLANT

(75) Inventor: Blayne A. Roeder, Lafayette, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/486,603

(22) Filed: Jun. 1, 2012

(65) Prior Publication Data

US 2012/0310323 A1   Dec. 6, 2012

Related U.S. Application Data

(60) Provisional application No. 61/493,090, filed on Jun. 3, 2011.

(51) Int. Cl.
  A61F 2/84    (2006.01)
  A61F 2/966   (2013.01)
  A61F 2/07    (2013.01)
  A61F 2/95    (2013.01)

(52) U.S. Cl.
  CPC . *A61F 2/966* (2013.01); *A61F 2/07* (2013.01); *A61F 2002/9511* (2013.01)

(58) Field of Classification Search
  CPC ............. A61F 2/966; A61F 2/07; A61F 2/95; A61F 2/86; A61F 2002/9511
  USPC ..................... 623/1.11, 1.13, 1.15, 1.23, 1.16; 606/108
  See application file for complete search history.

(56) References Cited

U.S. PATENT DOCUMENTS

| | | | |
|---|---|---|---|
| 6,350,277 B1 * | 2/2002 | Kocur | 623/1.11 |
| 2004/0073289 A1 * | 4/2004 | Hartley | 623/1.13 |
| 2007/0043425 A1 * | 2/2007 | Hartley et al. | 623/1.12 |
| 2007/0233223 A1 | 10/2007 | Styrc | 623/1.11 |
| 2010/0114290 A1 * | 5/2010 | Rasmussen et al. | 623/1.11 |

FOREIGN PATENT DOCUMENTS

| | | |
|---|---|---|
| GB | 2464978 A | 5/2010 |
| WO | WO 2006/007389 A1 | 1/2006 |
| WO | WO 2011/062858 A1 | 5/2011 |

OTHER PUBLICATIONS

European Search Report from corresponding EP 2529705 dated Sep. 28, 2012 (3 pages).

* cited by examiner

*Primary Examiner* — Thomas McEvoy
*Assistant Examiner* — Julie A Szpira
(74) *Attorney, Agent, or Firm* — Brinks Gilson & Lione

(57) ABSTRACT

An introducer system includes a release wire and wire receivers forming a constraining mechanism that facilitates constraining at least one segment of an implant while permitting the remainder of the implant to expand during deployment. The constrained segment includes wire receivers associated with the implant that couple to the release wire and hold the constrained segment in its constrained state until it is released to expand.

17 Claims, 9 Drawing Sheets

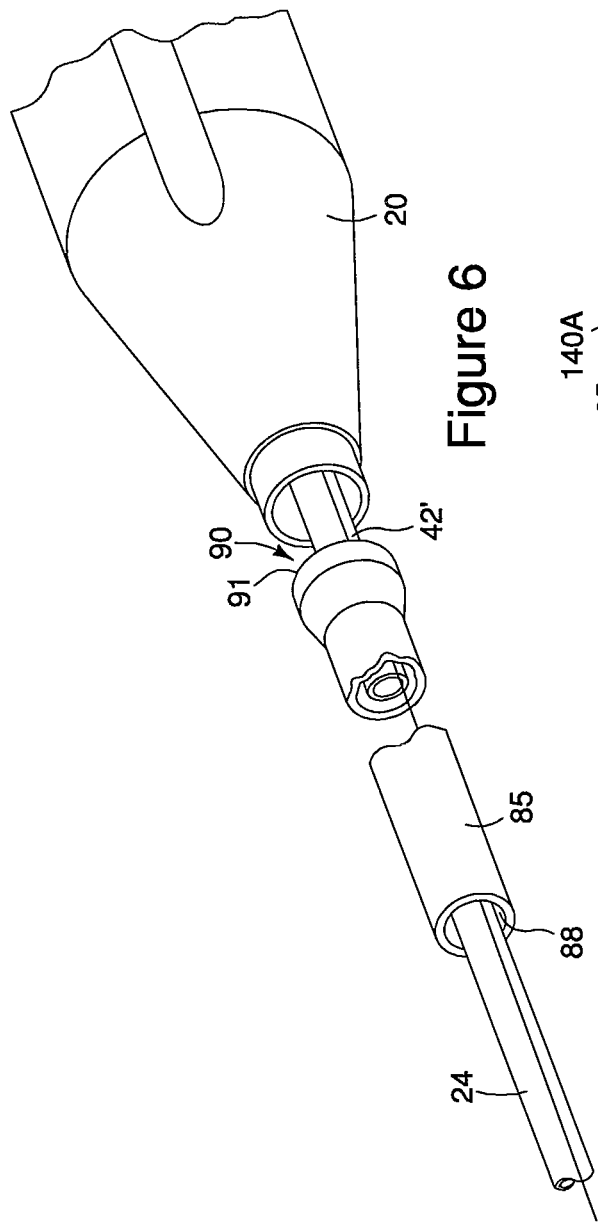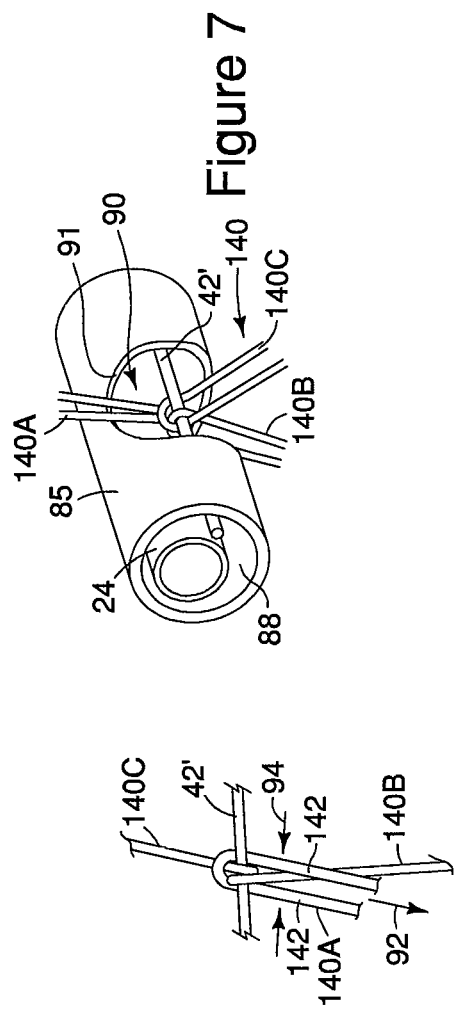

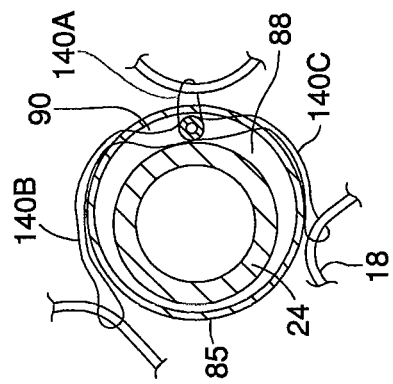
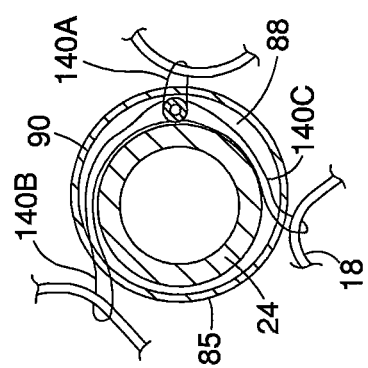
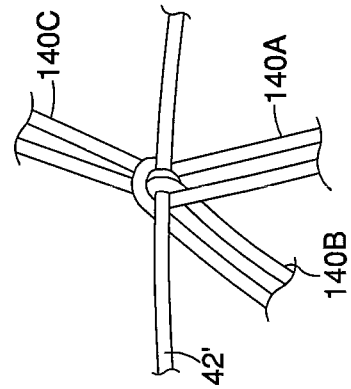
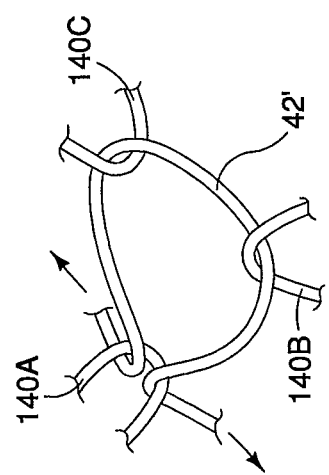
Figure 11B
Figure 9
Figure 11A
Figure 8

INTRODUCER FOR DEPLOYING AN IMPLANT

This application claims priority to provisional application 61/493,090 filed on Jun. 3, 2011, the complete disclosure of which is incorporated herein by reference in its entirety.

BACKGROUND

The present invention relates to an introducer for deploying an implant within a body lumen, such as a curved lumen. It also relates to a method of deploying an implant within a curved lumen.

Stent grafts are used to replace or repair vessels of the body such as the arteries. A stent graft is usually formed from a tubular body of a biocompatible graft material with one or more stents mounted into or onto the tubular body to provide support therefor. The stents may be balloon expandable stents and/or self-expanding stents.

Endovascular methods have been proposed for treatment of an aneurysm of the aorta particularly where the aneurysm is adjacent the aorta bifurcation. However, when an aneurysm occurs higher up in the aorta, in the region of the descending aorta adjacent the thoracic arch or in the ascending aorta, endovascular techniques for treating these aneurysms are somewhat more difficult because of the tight curvature of the thoracic arch, the occurrence of major arteries in the region, and the proximity to the heart. Placement of a substantially cylindrical prosthesis in such a curved region can cause problems.

Stent grafts are typically deployed using endovascular techniques from an introducer device in which the stent graft is retained in a radially contracted condition by an outer sheath. Portions of the stent graft may be retained in the contracted condition by a release arrangement. Typically, the release arrangement includes a plurality of release wires, such as three release wires extending through a cannula, that can be attached to connecting members between the stent graft and the release wires. A plurality of release wires along the circumference of introducer device takes up a certain volume and limits the minimum achievable delivery profile of the introducer device. Further, loading and/or aligning each release wire with each connecting member makes manufacturing and assembly complicated. A single connecting member receiving a single release wire provides substantial stress along the release wire, causing deformation to the wire in the form a bends. Thus, the release wire is typically sized larger than necessary to withstand such stress and deformation. Moreover, the connecting members are typically free to slide along the release wire, thereby undesirably introducing stress to the cannula surrounding the release wires. Further, sliding connecting members can induce segments of the stent graft prematurely tilt or rock in undesirable and less predictable deployment configurations, which can increase the risk of unsuccessful implantation of the stent graft along the vessel wall.

Upon withdrawal of the sheath and release of any retention arrangement where provided, for example in cases in which the stent graft has self-expanding stents, the stent graft can expand under the action of the self-expanding stents towards the vessel wall to redefine the blood flow path. The introducer device is then withdrawn after deployment.

Currently, a stent graft is deployed in a curved lumen by causing the stent graft to follow the curvature imparted to the introducer device. However, this can result in the stent graft not sitting properly in the blood vessel and in the lumen of the prosthesis being closed off or reduced in diameter. Kinks can also occur along the length of the prosthesis and these can cause problems with restriction of flow in the lumen.

Furthermore, when deploying a stent graft that is substantially cylindrical in a curved aorta, there is a danger that the proximal end of the stent graft, i.e., the end nearest the heart, will not lie flat against the walls of the aorta. For example, the proximal end of the stent graft will not be positioned perpendicularly to the wall of the vessel. As a result, blood can flow underneath the edge of the proximal end of the stent graft, particularly on the inner side of the curve of the thoracic arch, and cause the stent graft to buckle and close off thereby causing serious problems.

In general, this application relates to the placement of prostheses in the aorta in the region known as the thoracic arch where the aorta leaves the heart and curves over in approximately a semi-circle to the descending aorta and then into the abdominal aorta and then into the lower limbs via the iliac arteries. The application is, however, not so restricted and can relate to placement of prostheses within or in place of lumens in any portion of a human or animal body, though it is particularly relevant to curved lumens, particularly tightly curved lumens. It would be desirable to minimize the overall delivery profile of the introducer device, to simplify loading of the release wire through the connecting members, and to provide a more predictable stent graft configuration prior to deployment and thus increase the risk for successful implantation of the stent graft.

BRIEF SUMMARY

In one embodiment, an introducer system for deploying an implant in a lumen of a body is provided. The implant has a proximal end and a distal end; a first constrained segment, which may include a proximal segment, a distal segment or both, and a second constrained. The system includes a carrier to which the implant is mounted. The implant has a first expanded condition, a second expanded condition; and a constraining mechanism constraining the second constrained segment, including a first release wire and wire-receivers. The wire-receivers are attached to the implant and may extend inwardly from an inner surface of the implant. The wire receivers are attached to the release wire. The wire-receivers and the first release wire together radially constrain the second constrained segment of the implant in the first condition. In the first condition, the first constrained segment(s) is expanded and the second constrained segment is constrained, and in the second condition both the first and second constrained segments are expanded. In this manner, implant has sequential expansion with the second constrained segment being expanded after expansion of the first constrained segment.

The introducer system may include an implant having a proximal end, a distal end, a proximal end segment, a distal end segment, and an intermediate segment disposed between the proximal end segments and distal end segments, a cannula to which the implant is mounted, and a release wire lumen, having an inner surface, an outer surface; and at least one aperture extending from the inner to the outer surface. The cannula to which the implant is mounted may include the release wire lumen or the release wire lumen may be provided in a separate catheter. The system includes a constraining mechanism including a release wire extending longitudinally within the lumen and at least one wire-receiver disposed on an inner surface of the implant and releaseably attached to the release wire through the at least one aperture. The wire-receivers and the release wire radially constrain intermediate segment independent of proximal and distal segments, such that in a first configuration at least one of the proximal and distal segments are in an expanded configuration and the intermediate segment is in a constrained configuration.

A method of deploying an implant also is provided. The implant may have a proximal segment, a distal segment, an intermediate segment and at least one wire receiver on an inner surface of the intermediate segment. The method includes delivering the implant to a site of deployment with an introducer. The introducer may include at least one release wire releaseably engaging the at least one wire receiver to hold at least a portion of the intermediate segment in a constrained configuration. The method further includes expanding at least one of the proximal segment and distal segment; and subsequently expanding the intermediate segment by disengaging the at least one release wire from the at least one wire receiver.

BRIEF DESCRIPTION OF THE DRAWINGS

Embodiments of the present invention are described below, by way of example only, with reference to the accompanying drawings, in which:

FIG. 6 is a perspective view of a distal end of the implant deployment device of FIG. 5 with a distal fastening arrangement without an implant;

FIG. 7 is a perspective partial view of a distal end of the implant deployment device of FIG. 5 with a distal fastening arrangement for an implant with wire receivers;

FIG. 8 illustrates a release wire being threaded through wire receivers;

FIGS. 9-10 illustrate the release wire and the wire receivers under tension;

FIGS. 11A-11B are cross-sectional views of the implant deployment device of FIG. 6, depicting wire receivers of an implant coupled to a release wire;

DETAILED DESCRIPTION OF THE DRAWINGS AND THE PRESENTLY PREFERRED EMBODIMENTS

Figure 1:
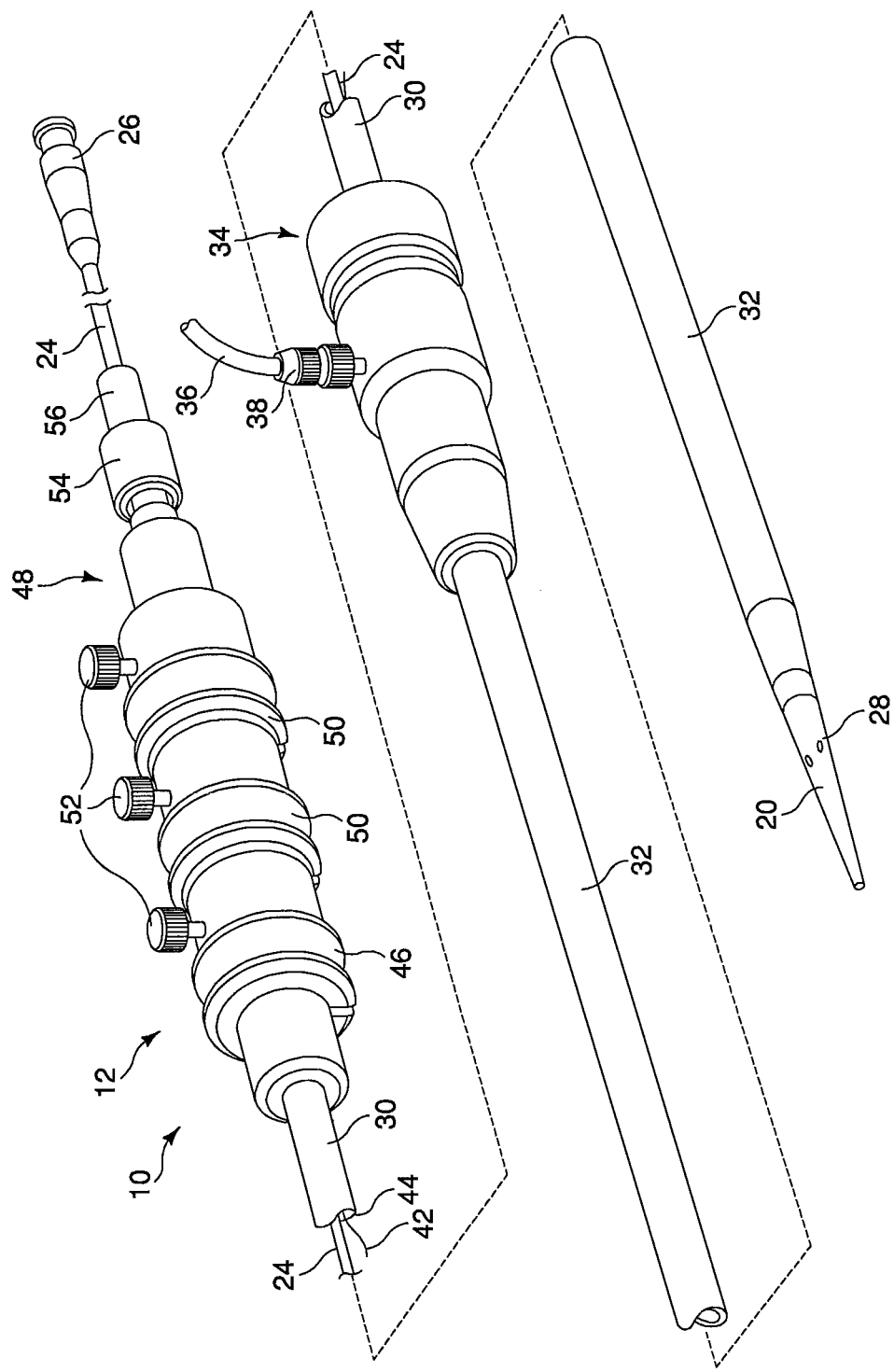
FIGS. 1 and 2 are perspective views of an example of an implant deployment device.

For the purposes of promoting an understanding of the principles of the present disclosure, reference will now be made to the embodiments illustrated in the drawings, and specific language will be used to describe the same. It is to be understood that the Figures are schematic and do not show the various components in their actual scale. In many instances, the Figures show scaled up components to assist the reader. It should also be noted that in the Figures like-referenced numerals designate corresponding components throughout the different views.

In the following discussion, the terms "proximal" and "distal" will be used to describe the opposing axial ends of the inventive sheath, as well as the axial ends of various component features. The term "proximal" is used in its conventional sense to refer to the end of the apparatus (or component thereof) that is closest to the operator during use of the apparatus. The term "distal" is used in its conventional sense to refer to the end of the apparatus (or component thereof) that is initially inserted into the patient, or that is closest to the patient during use.

Figure 2:
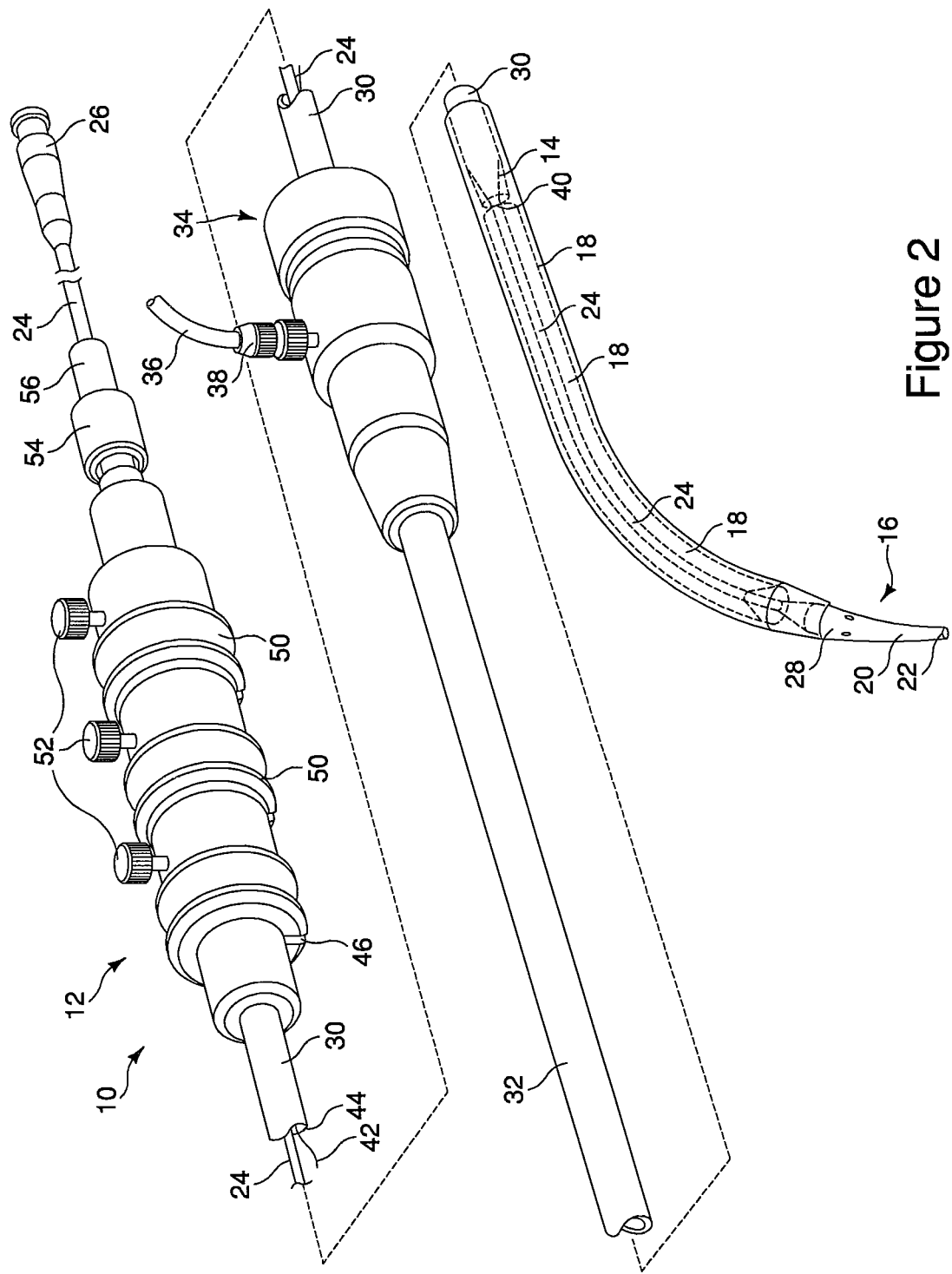

Referring to FIGS. 1 and 2, an implant deployment device 10 can include an external manipulation section 12, a proximal attachment region 14, and a distal attachment region 16. The proximal attachment region 14 and the distal attachment region 16 can secure the two ends of an implant 18. During the medical procedure to deploy the implant 18, the proximal and distal attachment regions 14 and 16 can travel through the patient's vasculature, in this example, to a desired deployment site. The external manipulation section 12 at the proximal end of the implant deployment device 10, which is operated by a surgeon to manipulate the introducer, remains outside of the patient throughout the procedure.

The distal attachment region 16 of the implant deployment device 10 can include a dilator tip 20, which is typically provided with a bore 22 therein for receiving a guide wire (not shown) of conventional type. The longitudinal bore 22 can also provide a channel for the introduction of medical reagents. For example, it may be desirable to supply a contrast agent to allow angiography to be performed during placement and deployment phases of the medical procedure.

An inner catheter or cannula 24, conventionally made from a flexible thin walled metal tube, can be fastened to the dilator tip 20. The inner catheter 24 is flexible so that the implant deployment device 10 can be advanced along a relatively tortuous vessel, such as a femoral artery, and so that the distal end of the implant deployment device 10 can be longitudinally and rotationally manipulated. The inner catheter 24 can form a carrier to carry the implant 18 or other device to be implanted in the patient. The inner catheter 24 can extend through the implant deployment device 10 to the manipulation section 12, terminating at a connection device 26, in conventional manner. The connection device 26 is designed to accept a syringe to facilitate the introduction of reagents into the inner catheter 24 and for this purpose is typically provided with a threaded luer lock connection.

Where provided, a pusher sheath or rod 30 (hereinafter referred to as a pusher member), typically made from a plastics material, can be mounted coaxial with and radially outside of the inner catheter 24. The pusher member 30 may be "thick walled," that is, the thickness of its wall is preferably several times greater than that of the inner catheter 24. In some instances, the pusher member 30 and the inner catheter 24 can be the same component, possibly having different outer diameters at the location at which the implant 18 is to be carried. A sheath 32 can be extended coaxially over and radially outside of the pusher member 30. The pusher member 30 and the sheath 32 extend distally to the manipulation region 12.

The implant 18, which may be a stent, a stent graft or any other implant or prosthesis deliverable by the implant deployment device 10, can be retained in a compressed condition by the sheath 32. The sheath 32 can extend proximally to a sheath manipulator and haemostatic sealing unit 34 of the external manipulation section 12. The haemostatic sealing unit 34 may include a haemostatic seal (not shown) and a side tube 36 held to the unit 34 by a conventional luer lock 38.

The sheath manipulator and haemostatic sealing unit 34 may also include a clamping collar (not shown) that clamps the sheath 32 to the haemostatic seal and a silicone seal ring (not shown) that forms a haemostatic seal around the pusher member 30. The side tube 38 can facilitate the introduction of medical fluids between the pusher member 30 and the sheath 32. Saline solution is typically used.

During assembly of the implant deployment device 10, the sheath 32 can be advanced over the proximal end of the dilator tip 20 of the proximal attachment region 16 while the implant 18 is held in a compressed state by an external force. A suitable distal attachment (retention) section (not visible in this view) can be coupled to the pusher member 30 and can retain a proximal end of the implant 18 during the procedure. The distal end of the implant 18 may be provided with a loop of material (not shown) through which a distal restraining wire 42 can be extended. The distal restraining wire 42 can also extend through an aperture (not shown in FIGS. 1 and 2) in the proximal attachment section 40 into an annular region 44 defined between the inner catheter 24 and the pusher member 30. The distal restraining wire 42 can extend through the annular space 44 to the manipulation region 12 and can exit the annular space 44 at a distal wire release mechanism 46.

A proximal portion of the external manipulation section 12 can include at least one restraining wire actuation section 50 mounted on a body 48, in turn mounted onto the pusher member 30. The inner catheter 24 may pass through the body 48. The distal wire release mechanism 46 and the proximal wire release mechanism 50 can be mounted for slidable movement on the body 48. Clamping screws 52 can prevent inadvertent early release of the implant 18. A haemostatic seal (not shown) is included so that the release wires can extend out through the body 48 without unnecessary blood loss during the medical procedure.

A proximal portion of the external manipulation section 12 can include a pin vice 54 mounted onto the proximal end of the body 48. The pin vice 54 can have a screw cap 56. When screwed in, vice jaws (not shown) of the pin vice 54 can clamp against or engage the inner catheter 24. When the vice jaws are engaged, the inner catheter 24 can only move with the body 48 and hence it can only move with the pusher member 30. With the screw cap 56 tightened, the entire assembly can be moved together as one piece.

Once the implant deployment device 10 is in the desired deployment position, the sheath 32 is withdrawn and the proximal and distal wire release mechanisms 50, 46 are released to allow the implant 18 to expand. For some procedures, the sheath 32 may be left in place after expansion of the implant 18. The pusher member 30 and inner catheter 24 may be withdrawn and replaced by a further component, using the sheath 32 as a guide.

Figure 3:
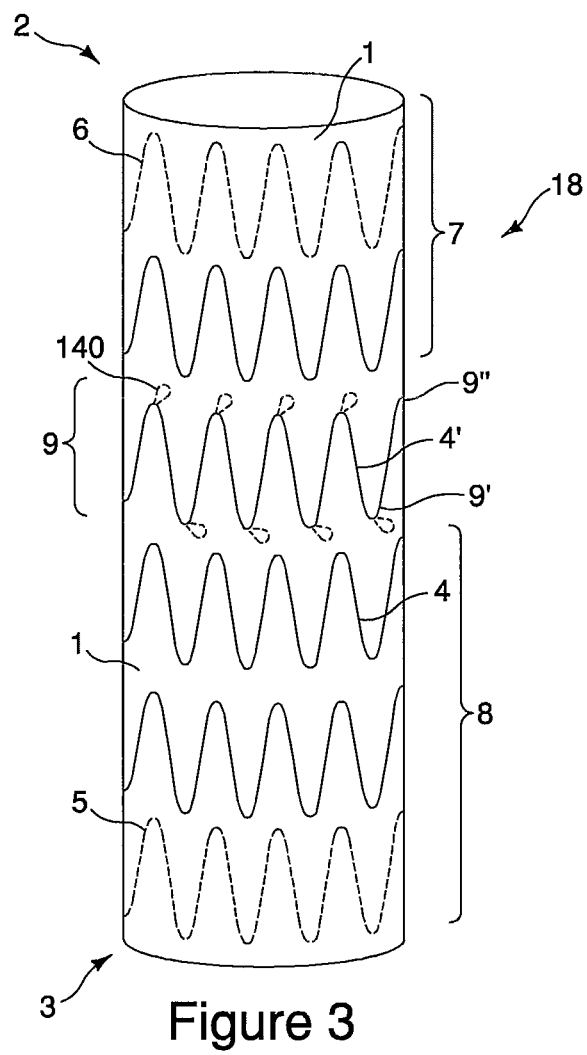
FIG. 3 is a perspective view of one example of an implant for deployment in a curved lumen.
Figure 4:
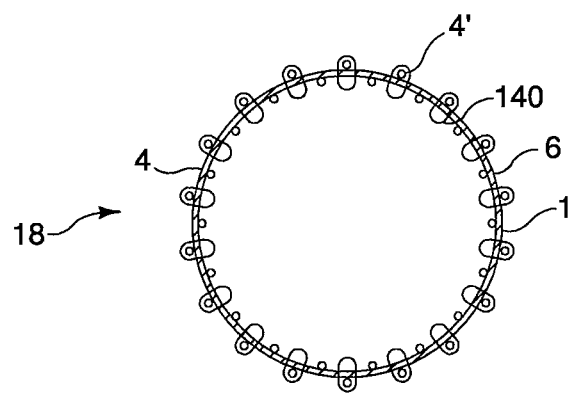
FIG. 4 is an end view of the implant of FIG. 3.

FIGS. 3-4 illustrate an example of the implant. As shown, the implant 18 comprises a biocompatible graft material tube 1, which can be substantially cylindrical. The graft material tube 1 can have a distal end 2 and a proximal end 3. The graft 1 can have a number of self-expanding zig-zag or well-known Gianturco Z-stents 4 positioned at intervals along the length of the graft 1 and configured to provide the force necessary to open the graft 1 out to the walls of the aorta when deployed. The stents may also be balloon-expandable as appreciated by those skilled in the art. In this example, six Z-stents 4, 4', 5, 6 are disposed along the length of the graft 1. In this embodiment, the stents 5, 6 disposed at the proximal end 3 and the distal end 2 of the tubular piece of graft material 1, respectively, are located on the inside of the graft 1, whereas the intermediate stents 4, 4' are located, e.g., in between the stents 5, 6, on the outside of the graft 1.

As shown in FIG. 3, the implant may include a distal segment 7, and proximal segment 8, and an intermediate segment 9. In this embodiment, the intermediate segment may be one of the stents 4'. The stent 4' may be located internally or externally of the intermediate segment 9. As shown, the intermediate segment 9 has wire-receivers 140. The wire receivers 140 may be part of stent 4' or attached to the inner surface of the biocompatible material. As shown in FIG. 3, the wire receivers may be loops. For example, the loops may be suture thread attached to the stent or the inner surface of the biocompatible graft material or loops integrally formed with the stent. As shown, wire receivers 140 can be provided on the proximal end 9' and/or the distal end 9'' of the intermediate segment 9, for instance, as shown here at the proximal end 9' and distal end 9'' of stent 4'. The wire receivers 140 may be provided at substantially equally spaced locations from one another around the inner surface of the intermediate segment of the implant. The wire receivers 140 are able to engage with a single release wire, such as, e.g., the release wire 42 of an introducer 10, for deployment of the implant 18.

In one example where wire receivers 140 are provided at both ends of the intermediate segment 9, the wire receivers 140 of the distal end 9'' of the intermediate segment 9 can engage a single release wire. The wire receivers 140 of the proximal end 9' of the intermediate segment 9 can engage the same single release wire or alternatively a second release wire to allow for independent expansion of the ends of the constrainable segment.

Figure 5:
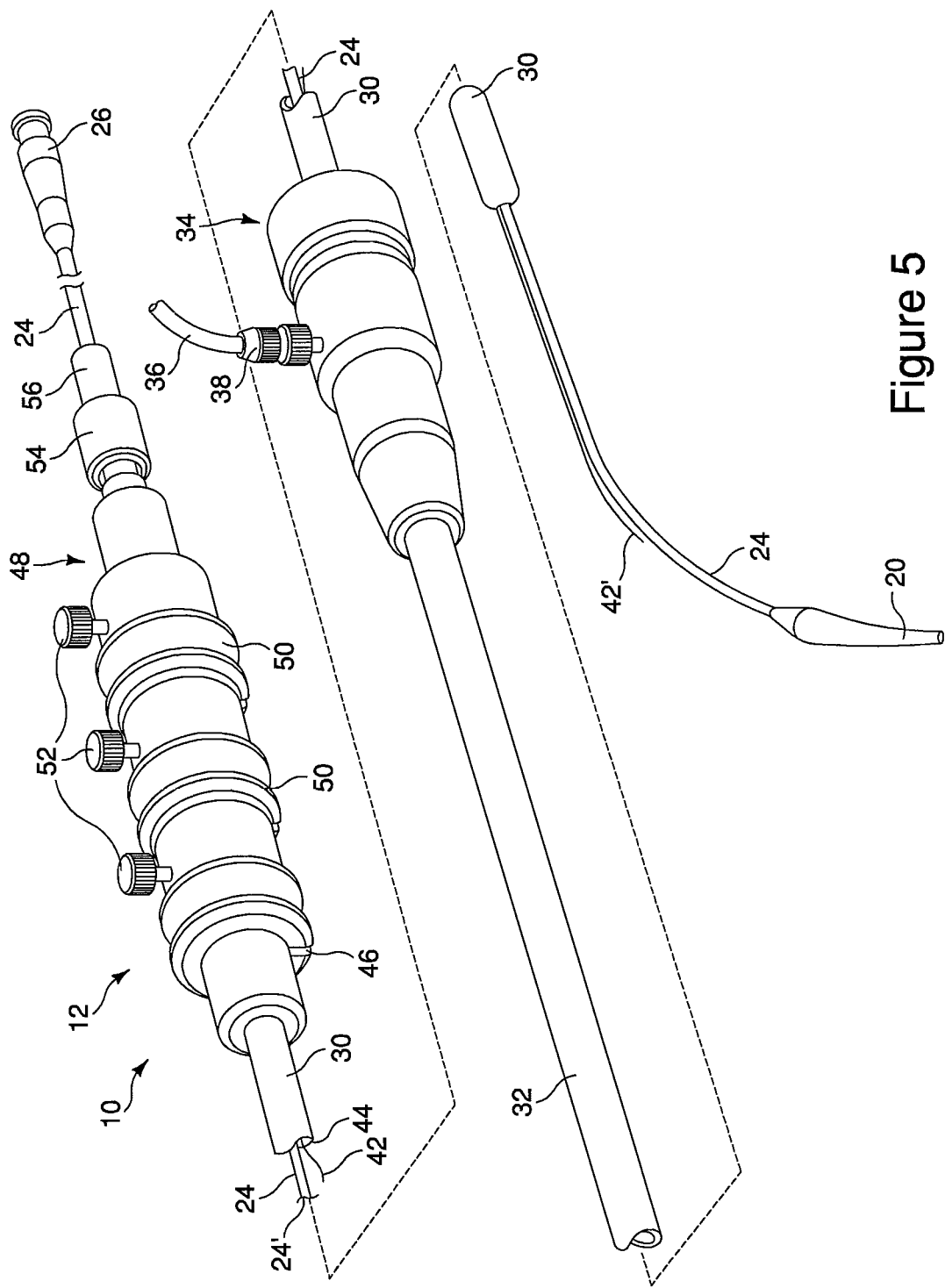
FIG. 5 is a perspective view of an example of an implant deployment device for deploying the implant of FIG. 3.

For deployment of the implant 18, the implant 18 is loaded in a radially compressed condition onto the carrier or inner catheter 24 of a deployment device 10' such as that shown in FIG. 5. The introducer 10' is similar to that shown in FIGS. 1-2. The introducer 10' includes a single release wire 42' able to engage with the wire receivers 140 of the implant 18. Together the release wire 42' and the wire receivers 140 comprise a restraining mechanism for the intermediate segment 9 of the implant. The wire receivers 140 can be provided on the graft material 1 instead of on the constrained stent 4'. The wire receivers 140 can additionally or alternatively be provided to co-operate with a release wire outside the tubular graft 1 instead of inside. The compressed implant 18 is then covered by the sheath 32 in a conventional manner for deployment.

FIG. 6 illustrates a distal part of the introducer 10'. The introducer 10' includes the inner catheter 24 extending to the dilator tip 20. A release wire catheter 85 can extend over the inner catheter 24 to the dilator tip 20 in a spaced relationship therebetween to define a release wire chamber 88 that allows for the passage of the release wire 42' therethrough. In addition, the inner lumen 24' of inner catheter 24 may comprise the release wire catheter. The distal end of the release wire 42' can be releasably attached to the dilator tip as can be appreciated by those skilled in the art. The release wire catheter 85 can form a shield about the release wire 42' for protection when moving the release wire 42' relative to the release wire catheter 85. An aperture 90 can be formed in the wall of the release wire catheter 85 and be in communication with the release wire chamber 88. The aperture 90 is sized to permit access between the wire receivers 140 of the implant 18 and the release wire 42'. The proximal end of the release wire 42' can be coupled to a wire release mechanism, such as, e.g., one of the wire release mechanisms 46 or 50, and can continue through the release wire chamber 88 to terminate within the region of the dilator tip 20. When it is desired to release the release wire 42' from engagement with the wire receivers 140, the release wire 42' can be pulled out from the proximal end of the introducer 10'.

FIGS. 7-10 show in further detail the engagement between the wire receivers 140 and the release wire 42'. The wire receivers 140 are shown to include three wire receivers 140A, 140B, and 140C, although one, two, four or more wire receivers can be provided as can be appreciated by those of ordinary skill in the art. The engagement between the release wire 42' and the wire receivers 140 is such that the wire receivers are inhibited from sliding independently relative to one another and/or the release wire catheter 85.

FIG. 8 illustrates one example of such non-slidable engagement. An end of the release wire 42' can be inserted through a first of the wire receivers in a first direction, such as the wire receiver 140A. The release wire 42' can be threaded through the next adjacent wire receiver in a single direction, such as the wire receiver 140B, and threaded through the next adjacent wire receiver in a single direction, such as the wire receiver 140C, and through more wire receivers in a single direction if present. The release wire 42' can be then returned to the first of the wire receivers, such as the wire receiver 140A, in a second direction, opposite the first direction. As can be appreciated, the release wire 42' can be sufficiently flexible to achieve such configuration. As a result, loading and/or threading the single release wire through each wire receiver can simplify manufacturing and assembly of the deployment device when compared to loading and aligning multiple release wires within the wire receivers.

In FIGS. 9-10, the release wire 42' is straightened when tension is applied thereto, and tension is applied to the wire receivers, thereby causing the ends of the wire receivers 140A, 140B, 140C to tighten around the release wire 42'. The legs 142 of the wire receiver 140A are positioned on the outside to capture the bodies of the wire receivers 140B, 140C between the legs. To this end, tension applied to the wire receiver 140A, represented by an arrow 92, can draw the legs 142 in a direction closer to one another, represented by arrows 94, to further increase the contact pressure and friction on the wire receivers 140B, 140C located in between the legs. This arrangement can inhibit the wire receivers from sliding independently relative to one another and/or the release wire catheter. This lack of slidability of the wire receivers can reduce undesirable stresses to the release wire. The stresses can lead to deformation of the release wire to cause premature tilting or rocking of the deployment arrangement of the implant. This lack of slidability of the wire receivers can prevent relative axial displacement between the wire receivers along the release wire, which can permit the constrainable segment from prematurely tilting or rocking. Such non-slidable engagement can facilitate in fixing the deployment arrangement of the implant and allow the deployment arrangement of the implant to be more predictable, which can increase the risk for a successful implantation of the implant along the vessel wall.

The aperture 90 can have various configurations to allow the wire receivers to extend radially into the release wire catheter and circumferentially about the release wire 42'. For example, the aperture 90 can be formed in the wall of the release wire catheter 85, as shown in FIG. 7, such that edges 91 define the aperture. The aperture 90 may be formed as the spacing between the edges 91 of separated discrete segments of the release wire catheter, as shown in FIG. 6. Where the wire receivers are disposed along different axial positions of the implant, such as the proximal and distal ends of the stent 4', additional apertures or segments may be provided in the release wire catheter for allowing the two or more sets of wire receivers to pass through, although the two sets of wire receivers can pass through a common aperture.

FIGS. 11A-11B depict examples of an arrangement in which the wire receivers, such as wire receivers 140A, 140B, 140C, can be pulled into the center of the implant 18. Three wire receivers can be spaced equidistantly from each other at about 120 degrees around the inner circumference of the implant about release wire catheter. If more than three wire receivers are present, the wire receivers can be spaced equidistantly from each other at substantially equal angles around the inner circumference of the implant. The wire receivers can be pulled within the release wire chamber 88 of the release wire catheter 85 through the aperture 90. Depending on the size of the aperture 90, the wire receivers 140B, 140C may extend directly into the aperture and lie against the inner cannula 24, as shown in FIG. 11A, or the wire receivers may extend along the circumference of the release wire catheter 85 for a distance before entering into the aperture, as shown in FIG. 11B. The release wire 42' may be placed at any location along the circumference of the inner catheter 24. The overall length of the wire receivers can vary depending on the relative position between each wire receiver and the release wire 42'. For example, the wire receiver closest to the release wire, e.g., the wire receiver 140A, can have the shortest length, whereas the other two wire receivers 140B, 140C can have a longer length. The use of a single release wire can take up a smaller volume to reduce the cross-sectional area of the release wire catheter, thereby reducing the delivery profile of the introducer device when compared to the use of a plurality of release wires, such as three release wires.

The wire receivers in tension apply shear forces in different radial directions around the circumference of the single release wire to prevent deformation of the release wire. In one example, the wire receivers are placed radially from each other so that the shear force caused by one wire receiver in tension, such as, e.g., the wire receiver 140A, in a first radial direction is counteracted by the shear force of one or more wire receivers, such as, e.g., the wire receivers 140B, 140C, in tension in a second radial direction opposite to the first radial direction. The counteracting forces from each of wire receivers decrease the overall concentrated stress to the release wire when compared to only a single wire receiver applying a concentrated shear force to a single release wire in a radial direction that can deform the wire. With a decrease in overall stress, a single release wire smaller in cross-sectional area, such as, e.g., less than 0.011-inch diameter, may be used.

Figure 12:
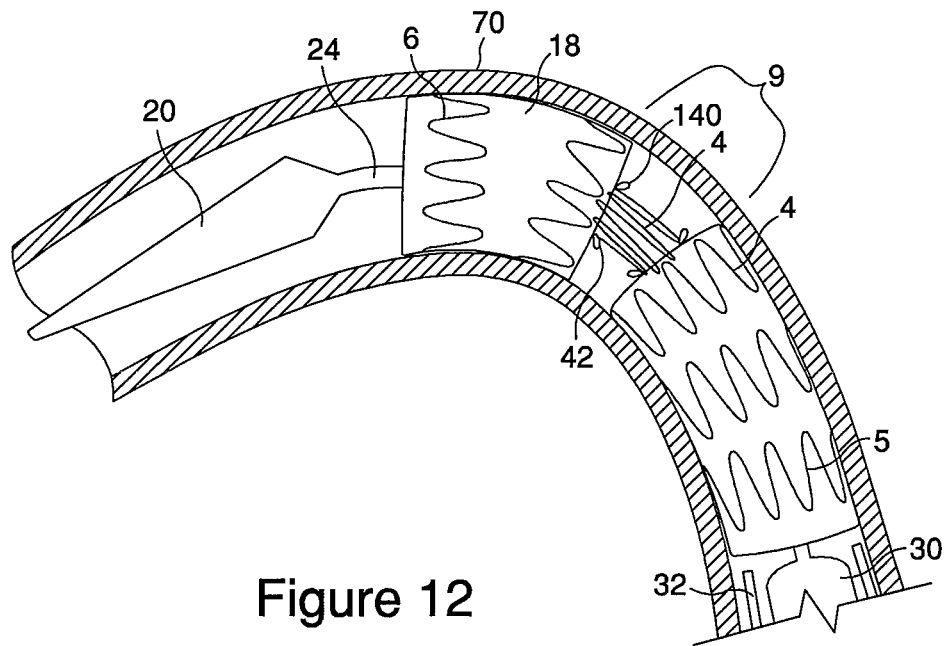
FIGS. 12-13 show deployment of the implant of FIG. 4 in a curved body lumen.

In FIG. 12, the implant 18 is delivered to the site of deployment, which in this example is within a curved body lumen (such as the thoracic arch). Once the implant deployment device 10 is in the desired deployment position, the sheath 32 can be withdrawn and the implant 18 is allowed to expand. However, the engagement between the release wire 42' and the wire receivers 140 can retain the constrained intermediate segment 9 of the implant 18, such as a single stent 4', in a constrained configuration. The intermediate segment 9, such as constrained stent 4', can be typically constrained by over about 50% of its expanded configuration, and may be constrained by up to about 70% or about 80%. This can depend upon the interval spacing between the stents. The intermediate segment 9, such as constrained stent 4', can be kept in its fully constrained condition around the inner catheter 24 of the implant deployment device 10. In one example, the constrained stent 4' may be expanded partially prior to release of the constraining mechanism. In another example, partial expansion of the constrained stent 4' can permit expanding to no more than 50% of its fully deployed diameter.

Next, the release wire 42' can be released from the wire receivers 140 to allow the constrained stent 4' to expand. Because of the non-slidable engagement between the wire receivers 140 and the release wire 42', the wire receivers can move with the release wire during withdrawal of the release wire in the proximal direction. The edges 91 that define the aperture 90 can contact the moving wire receivers 140 and stop the wire receivers relative to the moving release wire 42' to permit the release wire to be removed from the wire receivers. In one example, the edges 91 that define the aperture 90 can be modified, such as rounded, to prevent cutting of the wire receivers 140. The edges 91 may have a coating, such as an elastomer or silicone, applied thereto to soften the edges 91 that define the aperture 90 to prevent cutting of the wire receivers.

Figure 13:
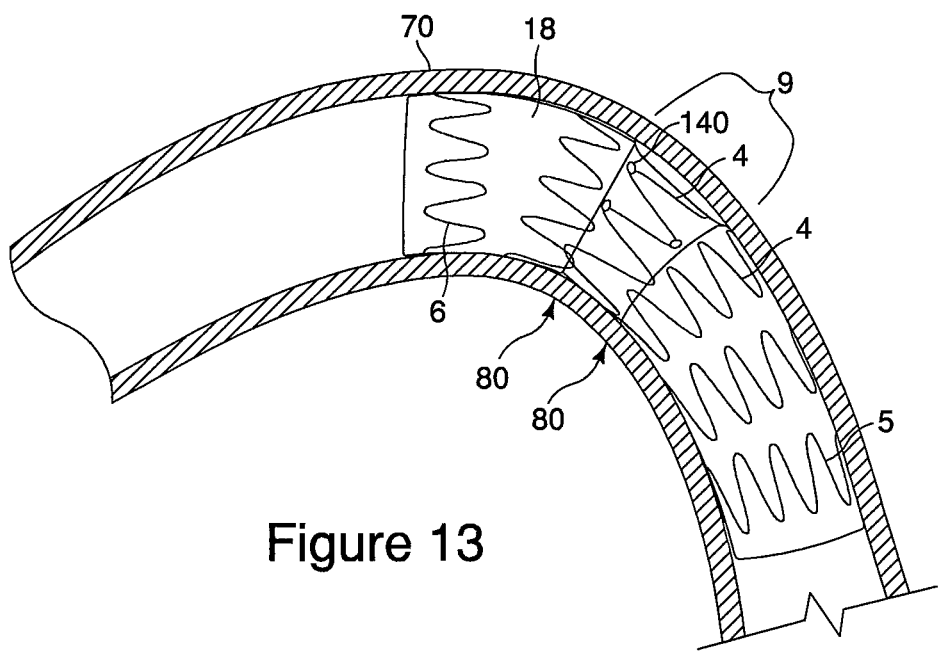

In FIG. 13, once the constrained stent 4' has expanded, the pusher member 30 and inner catheter 24 may be withdrawn leaving the expanded implant 18 in place. FIGS. 12-13 illustrate the improved positioning effect of this deployment process. FIG. 12 shows the implant 18 can be partially expanded after withdrawal of the sheath 32. Only the constrained stent 4' can remain in its compressed state by means of the release wire 42' and the wire receivers 140. The implant 18 can be located such that the constrained stent 4' is positioned at the tightest part of the bend of the curved body vessel 70. As such, the stents 4, 5, 6, which are allowed to expand as soon as the sheath 32 is withdrawn, engage against the walls of the body vessel 70 effectively because the vessel is not too relatively curved at the location where the stents 4, 5, 6 of the expanded portion are located.

FIG. 12 illustrates that the stent 4 that is located immediately proximally of the constrained stent 4' and the stent 4 located immediately distally of the constrained stent 4' can be positioned to be closer together on the inside part of the curved body lumen 70 than on the outside part of the curved body lumen. This may result from the constrained stent 4' drawing the graft material 1 and the adjacent stents 4 toward the constrained stent. As a result, the adjacent stents 4 can be located within the vessel 70 closer together on the inside part of the curved lumen than would be if the stent 4' between the adjacent stents 4 had not been constrained whilst expanded. Thus, when the constrained stent 4' is allowed to expand, the stent 4' overlaps with the adjacent stents 4 on the inside of the curve of the curved body vessel 70 at overlapping regions 80. One reason for the formation of overlapping regions 80 is that the gap between the adjacent stents 4 at deployment is less than the length of the constrained stent 4'. Further, the adjacent stents 4 can be allowed to expand first and properly engage the wall of the vessel 70, before expansion of the constrained stent 4' to engage with the interior of the adjacent stents 4 to form the overlapping regions 80.

Figure 14:
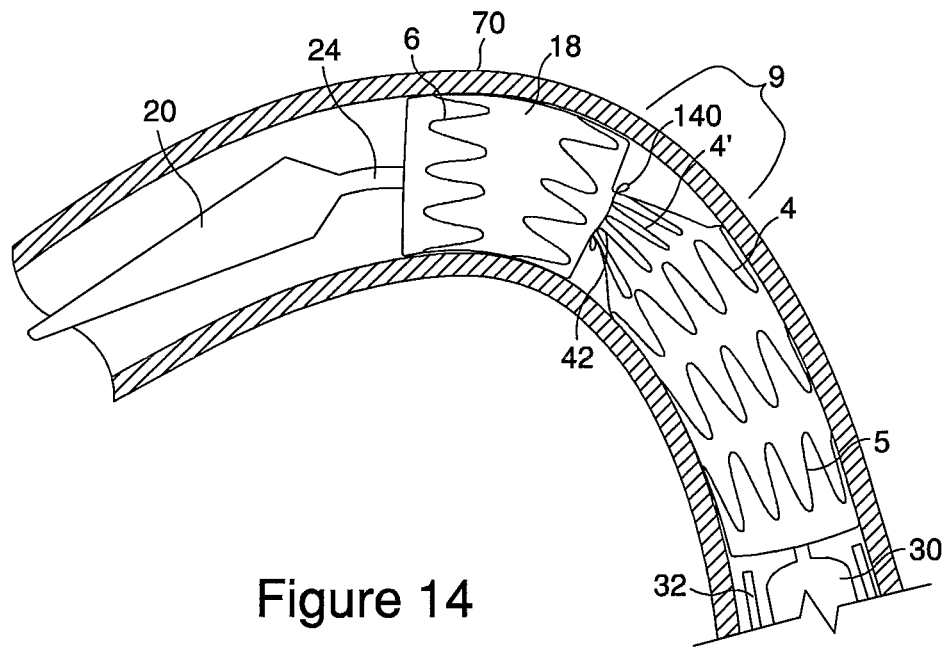
FIGS. 14-15 show deployment of another example of an implant in a curved body lumen.
Figure 15:
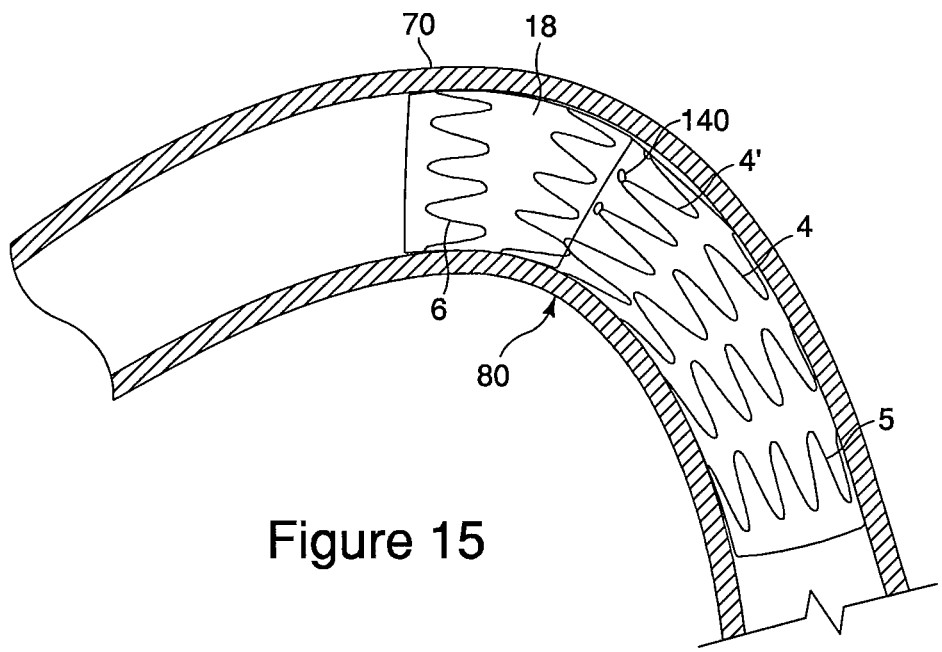

FIGS. 14-15 illustrate a second embodiment of the constraining mechanism. The difference here is that the constrained stent is constrained only at its distal end so that the constrained stent forms a "cone-shape" prior to release, but after expansion of the remainder of the implant 18. Again, when the constrained stent 4' is allowed to expand by removal of the release wire 42' from the wire receivers 140, the constrained stent 4' can expand to overlap with the interior of the stent 4 immediately distal to the constrained stent 4'. As shown in FIG. 15, the result is a single region of overlap 80 between the constrained stent 4' and its immediately distal stent 4. Constraining only the distal end of the constrained stent 4' can provide a positioning of the implant 18 that can maximize blood flow through the implant 18 after deployment.

Figure 16:
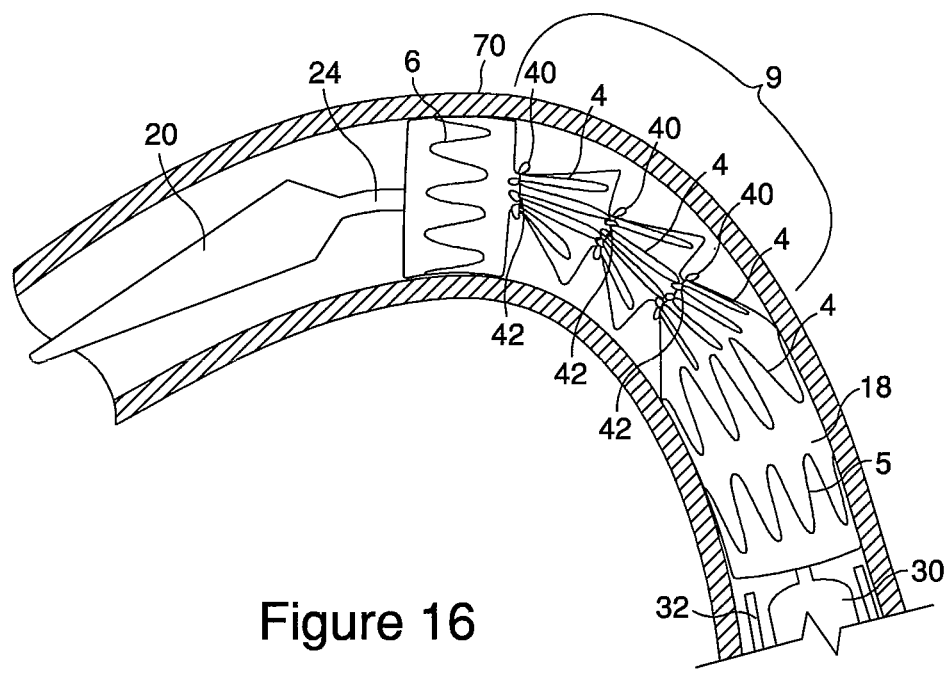
FIGS. 16-17 show deployment of another embodiment of an implant in a curved body lumen.
Figure 17:
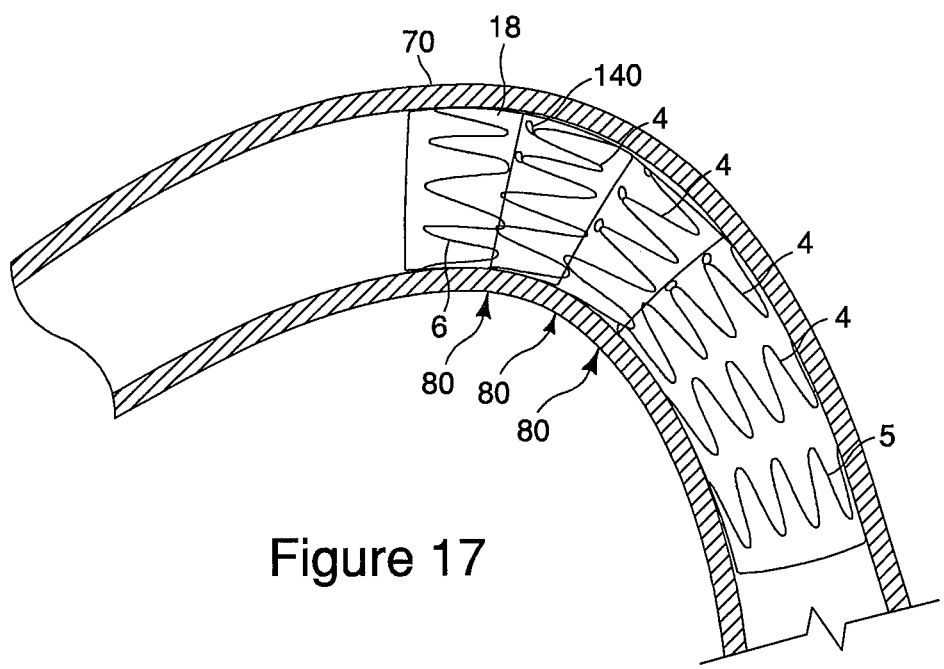

FIGS. 16-17 illustrate a third embodiment of the constraining mechanism. Here, more than one constrained stent 4', comprising the intermediate segment 9, is provided with wire receivers 140. Each constrained stent 4' may include wire receivers 140 at both its proximal ends and distal ends (and in particular, where two adjacent constrained stents 4' are provided) each constrained stent 4' is provided with wire receivers only at one end, in this example, the distal ends. As illustrated in FIG. 17, this arrangement leads to a plurality of regions of overlaps 80 with constrained stents 4' overlapping with the interior of an immediately distal stent 4, 6.

An advantage of the above-described embodiments is that a substantially cylindrical straight implant 18 can be deployed in a curved vessel. The stents 4 adjacent the intermediate segment 9 expand first and are properly anchored within the vessel without the need to match the curve of the implant to the lumen either prior to, or during, deployment. As the intermediate segment 9 expands during a second stage of deployment, the implant 18 can be used in any type of vessel, whether straight, having only a slight bend, or having a sharp bend. Proper curvature of the implant 18 within the vessel is therefore obtained. In addition, the curve of the implant 18 does not have to be matched to the curve of the vessel prior to deployment. Furthermore, the surgeon or clinician does not have to ensure that the implant is deployed in a particular orientation to match the curve of the vessel as is the case with prior art prostheses. Constraining the intermediate portion 9, such as stent 4', can create a neck portion, which imparts increased flexibility to the implant 18. This can assist in enabling the implant 18 to conform to the curvature of a vessel 70 irrespective of the extent of the curvature of the vessel. Furthermore, the implant can be accommodated within a curved lumen without the stents bunching together and creating gaps that might cause blood leakage. In one example, the constrainable stent is not the most proximal stent of the implant or the most distal stent of the implant. This assists in enabling the ends of the implant to be securely anchored within the vessel.

A constrained stent 4' may be combined within a single implant 18 where appropriate. In other embodiments, a constrained stent 4' may be located at any point along the implant 18, depending on the particular requirements. For example, the constrained stent 4' may be at the proximal end, in the middle, or in any one or more of the stents along the implant 18. In another modification, it is contemplated that every stent of the implant 18 could be constrained, preferably only at one end of each stent, which would preferably be at the distal end of each stent 4'. In one example, the constrained stent 4' is not the stent 6 at the distal end 2 of the implant 18. This is because the stent 6 at the distal end 2 of the implant 18 can be useful for anchoring and positioning of the implant 18.

In another modification, the release wire 42' may be the same as the wire 42 that holds the distal end of the implant to the distal end of the introducer.

In another modification, the wire receivers 140 of different constrained stents 4' can co-operate with different release wires 42'. For example, a single release wire 42' can be coupled to the wire receivers at a distal end of the constrained stent 4', while a single release wire can be coupled to the wire receivers at a distal end of the constrained stent. This enables greater control over the deployment process where desired by allowing different constrained stents 4' to be released in a particular desired order.

The term "thread" as used herein is intended to include any filamentary material which can perform the stated function and could, for example, be of conventional suture material, a multi-filamentary structure formed of yarns for example and of a natural or synthetic material such as cotton, other biocompatible material or a polymer material such as polyester, or a mono-filamentary structure of a natural material, other biocompatible material, a metal such as gold or an alloy such as Nitinol.

The features of the various embodiments described above and their modifications may be substituted for or combined with one another as desired. It is also to be understood that the various features of the dependent claims appended hereto may be used with one another in any desired combination of those claims.

Drawings in the figures illustrating various embodiments are not necessarily to scale. Some drawings may have certain details magnified for emphasis, and any different numbers or proportions of parts should not be read as limiting, unless so-designated in the present disclosure. Those skilled in the art will appreciate that embodiments not expressly illustrated herein may be practiced within the scope of the present invention, including those features described herein for different embodiments may be combined with each other and/or with currently-known or future-developed technologies while remaining within the scope of the claims presented here. It is therefore intended that the foregoing detailed description be regarded as illustrative rather than limiting. And, it should be understood that the following claims, including all equivalents, are intended to define the spirit and scope of this invention.

The invention claimed is:

1. An introducer system for deploying an implant in a lumen of a body, comprising:
    a self-expanding implant comprising:
    a proximal end and a distal end; a lumen extending between the proximal end and the distal end;
    a first segment having a constrained configuration and an expanded configuration;
    a second segment having a constrained configuration and an expanded configuration adjacent the first segment;
    a carrier to which the implant is mounted;
    a release wire catheter;
    and a constraining mechanism constraining the first segment, including a first release wire and circumferentially spaced wire-receivers, the wire-receivers attached to the first segment and extending inwardly from an inner surface of the first segment and releasably engaged to the first release wire;
    wherein the wire-receivers and the first release wire together radially constrain the first segment of the implant in its constrained configuration; and wherein in a first configuration of the implant, the second segment is expanded and the first segment is constrained, and in a second configuration of the implant, both the first and second segments are expanded, and
    wherein the wire receivers are attached to the release wire such that the wire receivers are prevented from sliding independently relative to each other and the release wire catheter.

2. The introducer system of claim 1, wherein the wire receivers comprise at least one loop attached to the inner surface of the implant.

3. The introducer system of claim 1, wherein the wire receivers comprise a plurality of loops attached to the inner surface of the implant.

4. The introducer system of claim 1, wherein the first segment is radially constrained substantially along an entire circumference of the second constrained segment.

5. The introducer system of claim 1, wherein in the second configuration of the implant, the first and second segments are in an overlapping configuration.

6. The introducer system of claim 5, wherein the first segment lies at least partially within the second segment.

7. The introducer system of claim 1, wherein the wire receivers comprise distal and proximal wire receivers and the constraining mechanism further comprises a second release, and wherein the first release wire is associated with the distal wire receivers and the second release wire is associated with the proximal wire receivers.

8. The introducer system of claim 1, further including at least one internal stent disposed within the first segment, wherein the wire receivers comprise a portion of the internal stent.

9. An introducer system for deploying an
    implant in a lumen of a body, the introducer including:
    an implant having a proximal end, a distal end, a proximal end segment, a distal end segment, and an intermediate segment disposed between the proximal end segment and distal end segment;
    a cannula to which the implant is mounted,
    a release wire catheter,
    a release wire lumen having an inner surface, an outer surface; and at least one aperture extending from the inner to the outer surface; a constraining mechanism including a release wire extending longitudinally within the lumen and at least three wire-receivers disposed on an inner surface of the implant and releaseably attached to the release wire through the at least one aperture;
    wherein the at least three wire-receivers and the release wire radially constrain the intermediate segment independent of proximal and distal segments, such that in a first configuration at least one of the proximal and distal segments is in an expanded configuration and the intermediate segment is in a constrained configuration, and
    wherein the at least three wire-receivers are attached to the release wire such that the at least three wire-receivers are prevented from sliding independently relative to each other and the release wire catheter.

10. The introducer system of claim 9, wherein the at least one wire receiver comprises a plurality of wire receivers.

11. The introducer system of claim 10, wherein the plurality of wire receivers are disposed circumferentially about the inner surface of the intermediate segment.

12. The introducer system of claim 11, further comprising a plurality of apertures wherein the release wire is releaseably attached to the plurality of wire receivers through the plurality of apertures.

13. The introducer system of claim 9, where the wire receivers comprise loops.

14. The introducer system of claim 9, wherein the intermediate segment comprises an internal stent and wherein the wire receivers comprise portions of the internal stent.

15. The introducer system of claim 14, wherein the wire receivers comprise loops on the internal stent.

16. The introducer system of claim 9, wherein the intermediate segment comprises a proximal end and a distal end and the constraining mechanism constrains only one of the ends.

17. The introducer system of claim 10, wherein the intermediate segment comprises a proximal end and a distal end and the constraining mechanism constrains both of the ends.

* * * * *